United States Patent [19]

Berkowitz

[11] 4,298,764
[45] Nov. 3, 1981

[54] PREPARATION OF ALKYL GLYCERYL ETHER ALCOHOLS

[75] Inventor: Sidney Berkowitz, Highland Park, N.J.

[73] Assignee: FMC Corporation, Philadelphia, Pa.

[21] Appl. No.: 132,485

[22] Filed: Mar. 21, 1980

Related U.S. Application Data

[63] Continuation-in-part of Ser. No. 61,219, Jul. 27, 1979, abandoned.

[51] Int. Cl.$^3$ ............................................. C07C 41/03
[52] U.S. Cl. ................................... 568/618; 568/623; 568/679; 568/680
[58] Field of Search ................ 568/618, 623, 679, 680

[56] References Cited

U.S. PATENT DOCUMENTS

| 2,089,569 | 8/1937 | Orthner et al. | 568/679 |
| 3,719,636 | 3/1973 | Wojtowicz et al. | 568/618 |
| 4,105,580 | 8/1978 | Sebag et al. | 568/678 |
| 4,217,296 | 8/1980 | Berkowitz | 568/679 |

FOREIGN PATENT DOCUMENTS 420903  12/1934  United Kingdom ................ 568/679

Primary Examiner—Howard T. Mars
Attorney, Agent, or Firm—Christopher Egolf

[57] ABSTRACT

This invention relates to a process for preparing nonionic glycidol-derived surfactants. Specifically $C_{10}$-$C_{20}$ n-alkyl glyceryl ether alcohols containing from 1 to about 10 glyceryl units, are prepared by reacting crude glycidol and a $C_{10}$-$C_{20}$ n-alkyl alcohol in the presence of a non-polar, non-reactive miscible solvent.

13 Claims, No Drawings

PREPARATION OF ALKYL GLYCERYL ETHER ALCOHOLS

This application is a continuation-in-part of copending application Ser. No. 061,219 filed July, 27, 1979 and now abandoned.

The present invention relates to the preparation of nonionic glycidol-derived surfactants useful in formulating detergent compositions. More particularly, the invention relates to a process for producing $C_{10}$-$C_{20}$ n-alkyl glyceryl ether alcohols containing from 1 to about 10 glyceryl units by reacting crude glycidol and a $C_{10}$-$C_{20}$ n-alkyl alcohol in the presence of a solvent. The expression "$C_{10}$-$C_{20}$ n-alkyl alcohol" as used herein is understood to include mixtures of $C_{10}$-$C_{20}$ alcohols.

It is known that certain alkyl glyceryl ether alcohols may be prepared by reacting the corresponding aliphatic alcohol with glycidol. West German Pat. No. 2,657,517, to K. L. Jones, for example, broadly discloses that mono-glyceryl ethers of alkanols may be prepared by condensation of a higher alkanol with glycidol.

J. A. Wotjowicz et al, in U.S. Pat. No. 3,719,636, disclose a process for preparing $C_8$-$C_{26}$ aliphatic glyceryl ether alcohols containing 4-14 glyceryl units. The process involves reacting glycidol and the selected aliphatic alcohol, in a molecular ratio within the range of 4:1 to 14:1 respectively. The reaction is carried out in the presence of an acid or base catalyst, and a solvent which is polar, non-reactive, and miscible with the selected alcohol, glycidol and reaction product. Specific solvents disclosed as being suitable in carrying out the process are ketones, ethers, amides, and dioxolanes, the choice of the particular solvent depending upon the choice of catalyst. Yields on the order of 80–100% are reported in the examples of this patent. I, however, have not been able to duplicate such high yields in the base catalyzed solvent systems disclosed by this patent. (See Comparative Example B.)

Additionally, U.S. Pat. No. 4,105,580 to H. Sebag et al, discloses a process for preparing polyglycerol nonionic compounds by reacting, in the presence of a basic catalyst, certain organic compounds containing an active hydrogen with crude glycidol. (Crude glycidol is defined in U.S. Pat. No. 4,105,580 as the reaction mixture obtained from dehydrochlorination of glycerol monochlorohydrin and contains, in addition to glycidol, the solvent employed, the water formed during the course of the reaction or introduced with the reactants, the fraction of unreacted glycerol monochlorohydrin, small quantities of residual sodium chloride or potassium chloride and optionally products of hydrolysis or of polymerization of the thus produced glycidol.) Again, a polar solvent system is employed. The two solvents specifically disclosed are tert-butanol and isopropanol, the latter being especially preferred. No disclosure is made of yields obtained from the reaction of such crude glycidol and the active hydrogen-containing organic compound.

It has now been found that high yields of n-alkyl glyceryl ether alcohols of the general formula:

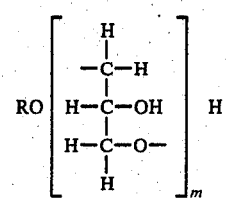

wherein R is a $C_{10}$-$C_{20}$ n-alkyl radical and m is a number from 1 to about 10 can be prepared by my process which comprises the steps of bringing together and reacting a $C_{10}$-$C_{20}$ n-alkyl primary alcohol and crude glycidol which is predissolved in a non-polar, non-reactive and miscible solvent selected from the group consisting of benzene, toluene, ortho-xylene, meta-xylene, para-xylene, and mesitylene, in the presence of a basic catalyst in a reaction zone, said alcohol and glycidol being brought together and reacted in a molecular ratio within the range of from about 1:0.9 to about 1:10; maintaining the resulting reaction mass in an agitated condition; maintaining the temperature of the reaction mass within the range of from about 125° to about 180° C. during the reaction period; separating said non-polar solvent from the reaction mass; and recovering a $C_{10}$-$C_{20}$ n-alkyl glyceryl ether alcohol product.

The expression "crude glycidol", as used in this disclosure, describes glycidol which is contaminated with glycerine.

Formation of the aforesaid $C_{10}$-$C_{20}$ glyceryl ether alcohols in the process of the invention may be said to progress stepwise as illustrated by the following equations showing formation of the lower molecular weight $m=1$-3 ether alcohols, wherein R is an n-alkyl radical containing from about 10 to about 20 carbon atoms and preferably 12 to 16 carbon atoms:

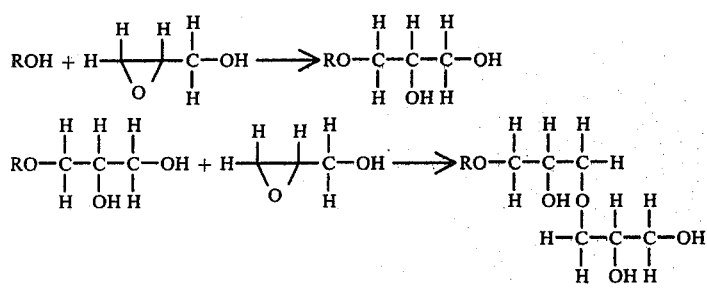

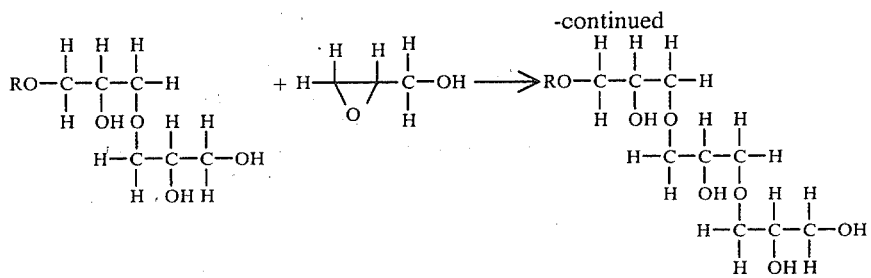
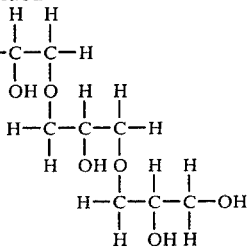

The n-alkyl glyceryl ether alcohols thus formed can be represented by the following general formula:

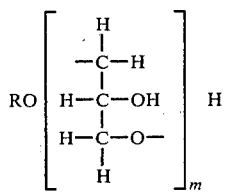

wherein R is an n-alkyl radical containing from about 10 to about 20 carbon atoms and preferably 12 to 16 carbon atoms, and m is a number from 1 to about 10.

The higher molecular weight compounds, containing more than 3 and up to about 10 glycidyl units, may also be formed, by adjusting the relative amounts of alcohol and glycidol reactants used.

The n-alkyl glyceryl ether alcohols produced by the process of the invention will undoubtedly contain positional isomers of the various glyceryl ether alcohols, and it is to be understood that herein and in the appended claims, any reference to the glyceryl ether alcohols is to be construed as including within its scope the positional isomers of said glyceryl ether alcohols. For example, the epoxy ring of the glycidol may break so that the ether linkage between the alcohol and glyceryl radical may attach to either the terminal or middle carbon of the glyceryl radical. Also, the attachment of the second glyceryl radical to the first may be through an ether linkage to the terminal or middle carbon atom. By way of illustration, four of the isomeric di-glyceryl ether alcohols may be illustrated by the following structural formulations:

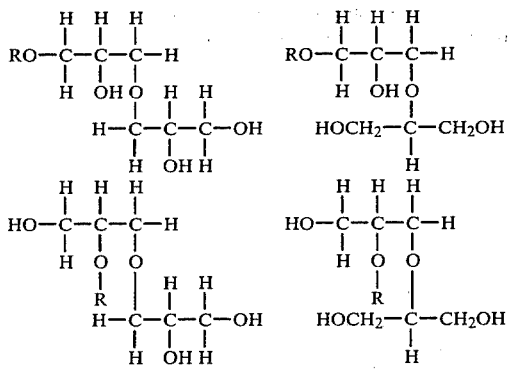

In carrying out the process of the invention, generally stoichiometric equivalents of the reactants are employed. When, however, it is desired to prepare the monomer and/or dimer ether alcohols (ether alcohols having 1 and 2 glycidyl units respectively) it is preferred to employ a 5–10% stoichiometric excess of alkyl alcohol to optimize product yields. Accordingly, molecular ratios within the range of from about 1:0.9 to about 1:10 of alcohol:glycidol are generally used.

Crude glycidol may contain at least 1% by weight glycerine, up to as much as 25% glycerine or more. Crude glycidol typically contains from about 5 to 20% by weight glycerine. Besides glycerine, crude glycidol often contains water and may in fact be an aqueous glycidol solution and may also contain unreacted reactants or byproducts of the glycidol manufacturing procedure employed.

Crude glycidol or aqueous solutions thereof may be produced by several manufacturing procedures, the amounts of glycidol, glycerine and water being dependent on the particular procedure employed. Crude glycidol can be prepared from the reaction of alkyl alcohol with an active oxygen-containing compound such as percarboxylic acid (peracetic acid) or hydrogen peroxide. Alternatively, crude glycidol can be made by the reaction of 1- or 2-glycerol monochlorohydrin with an alkali such as sodium hydroxide.

The crude glycidol reactant is dissolved in the non-polar, aromatic hydrocarbon solvent prior to its being contacted and reacted with the alkyl alcohol. The concentration of glycidol in such solvent, although not critical, is preferably from 5–50 weight percent, the most preferred range being from 10–20 weight percent.

The use of a non-polar solvent to predissolve the crude glycidol in the process of this invention has unexpectedly been discovered to provide marked advantages over the polar solvents employed in prior art methods. Non-polar solvents selected from benzene, toluene, xylene and mesitylene appear to selectively dissolve glycidol from crude glycidol solutions, rejecting the glycerine contaminant and water, if any.

When crude glycidol predissolved in the non-polar solvent is employed in the process of this invention, the reaction efficiency of the glycidol with the n-alkyl alcohol has been found to be superior to that of the corresponding reaction carried out with a polar solvent. Furthermore, detersive characteristics of the surfactant products obtained in the process of the invention are very superior to those of the reaction products obtained in analogous procedures employing a polar solvent.

The basic catalysts which may be used in preparing the alkyl glyceryl ether alcohols according to the invention, include the alkali metal hydroxides, for example, sodium hydroxide, potassium hydroxide and lithium hydroxide; the alkali metals, for example, sodium and potassium and the alkali metal alkoxides such as sodium methoxide and potassium ethoxide. The preferred basic catalyst is potassium hydroxide.

The amount of catalyst used will generally vary from 1 to 15% based on the amount of selected n-alkyl primary alcohol employed and preferably will vary from 4 to 12%.

The temperature at which the reaction is carried out will generally vary from 125° to 180° C. and preferably from 150° to 170° C.

Preferably, the reaction is carried out under an inert atmosphere, for example, a nitrogen atmosphere to prevent undesired glycidol side reactions.

Means are provided for maintaining the reaction mass in an agitated condition throughout the reaction period to facilitate contact between the reactants. Preferably, the degree of agitation provided is selected in coordination with the rate of addition of glycidol to reaction zone so as to minimize the presence of isolated concentrations of glycidol in the reaction zone which can lead, for example, to formation of undesired polyglycidol.

The aromatic hydrocarbon solvent is separated from the reaction mass, preferably by being distilled from the reaction mass during the reaction period (perferably continuously) in order to improve the efficiency of the reaction and simplify subsequent recovery of the product from the reaction mass.

The reaction time for obtaining good yield of $C_{10}$-$C_{20}$ n-alkyl glyceryl ether alcohols can vary from about 1 to about 6 hours, but it is generally from about 2 to about 3 hours, the time being primarily a function of the rate of distillation of the aromatic hydrocarbon solvent, the selected reaction temperature and the degree of agitation provided.

At the end of the reaction period, the reaction mass is preferably cooled and the alkyl glyceryl ether alcohol recovered therefrom. Preferably, such recovery involves dissolving the reaction mass in a suitable solvent or solvents (for example, chloroform, methylene chloride, dichloroethane, methanol and ethanol, methylene chloride being a particularly preferred solvent) and deactivating the basic reaction catalyst with a suitable acid salt (for example, sodium bisulfate monohydrate and sodium acid phosphate). The resulting product-containing mixture is then dried to remove moisture (generally with a dehydrating agent as magnesium sulfate or sodium sulfate) and filtered. The filtrate is distilled to remove the added work-up solvent and any unreacted alkyl alcohol overhead and recover the n-alkyl glyceryl ether alcohol product as bottoms.

The process can be carried out in a batch or continuous fashion, as desired.

The following examples are given to illustrate the invention and are not intended to be limitative thereof.

EXAMPLE 1

A 250 ml 3-necked flask, equipped with a Teflon paddle stirrer, thermometer, short path distillation column, condenser and self-equalizing dropping funnel was charged with 9.3 g (0.05 moles) of lauryl alcohol. One gram (0.018 moles) of powdered potassium hydroxide was added to the alcohol and the reaction mixture was heated with stirring to 155° C. A solution of 11.1 g (0.15 moles) glycidol (purity: 99.9%) in 100 ml of toluene was added dropwise over 2 hours. A nitrogen blanket was maintained over the resulting reaction mass throughout the reaction period. The toluene was continually distilled from the reaction mass. After the glycidol addition was completed, the reaction mass was stirred at 155° C. for an additional 30 minutes, then cooled to room temperature. The reaction mass was then dissolved in 50 ml of methylene chloride. Two and five tenths grams of sodium bisulfate monohydrate were added to the solution to deactivate the catalyst. The resulting product-containing mixture was dried over magnesium sulfate and filtered. The filtrate was distilled; the methylene chloride and unreacted alcohol were recovered overhead and the n-alkyl glyceryl ether alcohol product was recovered as bottoms. A utilization of 90% lauryl alcohol was obtained based on the amount of recovered lauryl alcohol (0.09 g). The product, a low melting solid, was analyzed by NMR spectroscopy and found to have an average molecular weight of 468 which corresponds to an average degree of polymerization of 3.8.

EXAMPLE 2

The procedure and equipment employed in this example were the same as in Example 1, except that 22.2 grams (0.3 moles) of glycidol (purity: 99.9%) were used in carrying out the reaction and 70 ml of a 50/50 mixture (volume percent basis) of methylene chloride and methanol were used as the solvent in the work-up of the reaction product. A utilization of 89% lauryl alcohol was obtained based on the amount of recovered lauryl alcohol (0.95 g). The product was analyzed by NMR spectroscopy and found to have an average molecular weight of 769 which corresponds to an average degree of polymerization of 7.8.

EXAMPLE 3

The procedure and equipment employed in this example were the same as in Example 1 except that 10.7 g (0.05 moles) of myristyl alcohol were charged into the flask. One gram (0.018 moles) of powdered potassium hydroxide was added to the alcohol and the reaction mixture was heated with stirring to 155° C. A solution of 11.1 g (0.15 moles) glycidol (purity: 99.9%) in 100 ml of toluene was added dropwise over 2 hours. The work-up of the reaction mixture was essentially the same as described in Example 2. A utilization of 88.8% myristyl alcohol was obtained based on the amount of recovered myristyl alcohol (1.2 g). The product was analyzed by NMR spectroscopy and found to have an average molecular weight of 500 which corresponds to an average degree of polymerization of 3.8.

EXAMPLE 4

The procedure and equipment employed in this example were the same as in Example 1 except that the glycidol (purity: 99.9%) was dissolved in 100 ml of orthoxylene. After work-up as described in Example 2, a utilization of 88.8% lauryl alcohol was obtained based on the amount of recovered lauryl alcohol (0.96 g). The product was analyzed by NMR spectroscopy and found to have an average molecular weight of 470 which corresponds to an average degree of polymerization of 3.8.

The following comparative examples, Examples A and B, demonstrate the lower yields obtained when employing a polar instead of a non-polar solvent.

COMPARATIVE EXAMPLE A

The procedure and equipment employed in this example were the same as in Example 1 except that the glycidol (purity: 99.9%) reactant was dissolved in the polar solvent methyl ethyl ketone instead of toluene.

A utilization of 57% lauryl alcohol was obtained based on the amount of recovered lauryl alcohol (4.0 g). The product, a low melting solid, was analyzed by NMR spectroscopy and found to have an average molecular weight of 438, which corresponds to an average degree of polymerization of 3.4.

COMPARATIVE EXAMPLE B

The procedure employed in this example was essentially that of Example I of U.S. Pat. No. 3,719,636. Nine and eight tenths grams (0.05 moles) of Alfol 1214 (55% $C_{12}$, 40% $C_{14}$), produced by Continental Oil Company were reacted with 38.4 g (0.52 moles) of glycidol (purity: 99.9%) dissolved in the polar solvent methyl ethyl ketone. The glycidol solution was added dropwise to a mixture of the Alfol and 1.08 g of powdered potassium hydroxide, over a period of 2.5 hours. The well-stirred reaction mixture was heated with an oil bath to 150°–155° C. under a slow nitrogen purge. Methyl ethyl ketone was distilled out continuously during the reaction. The product was stripped of volatiles using a nitrogen purge. A utilization of 58.2% Alfol was obtained based on the amount of recovered Alfol (4.2 g). The product was analyzed by NMR spectroscopy and found to have an average molecular weight of 926, which corresponds to an average degree of polymerization of 10.2.

EXAMPLE 5

This example is intended to demonstrate the detersive properties of products produced by the processes of the previous examples; the characteristics of these surfactant products are summarized in Table I-a. Accordingly, surface tension, foam height and foam half-life measurements were made on the n-alkyl ether alcohols obtained from Examples 1 through 4. For comparison purposes, the same measurements were made using a 1 to 4 adduct of lauryl alcohol and ethylene oxide (a nonionic surfactant commonly used in the industry) and the ether alcohols produced by Comparative Examples A and B.

The surface tension measurements were made using a Fisher Surface Tensiometer and are reported in Table I-b as dynes/cm at 23.5° C. Low values for this measurement are indicative of good detersive properties. Values between about 28 and 35 are generally desired for commercial use. As can be seen from the Table, the values for ether alcohols obtained from Examples 1 through 4 are within this range and compare favorably with the lauryl alcohol/ethylene oxide adduct used as a standard.

The foam height and foam half-life measurements were made following the Ross-Miles Test (ASTM Method D 1173-53). Values for these measurements are given in Table I-b. High values are desired as they are indicative of good foam stability. As can be seen from the Table, foam height (initial and after 5 minutes) and foam half-life values for the compounds from Examples 1 and 2 are appreciably greater than the corresponding values for the lauryl alcohol/ethylene oxide adduct used as a standard.

Additionally, a comparison of the foam height and foam half-life measurements of the lauryl ether alcohol products of Examples 1 and 4 (prepared using non-polar solvents) with those of the similar average molecular weight product of Comparative Example A (prepared using a polar solvent) shows considerably higher and thus superior values for the products produced according to Examples 1 and 4.

COMPARATIVE EXAMPLE C

The procedure employed in this example was essentially that of Example I of U.S. Pat. No. 3,719,636. However, the glycidol employed in this example was crude glycidol, which contained 80% by weight glycidol and 20% by weight glycerine.

A total of 24.0 g of crude glycidol, which contained 19.2 g glycidol (0.26 g-mole), was dissolved in 180 g methyl ethyl ketone solvent to form a clear solution. The glycidol solution was added dropwise, over a period of 2.5 hours, to 4.9 g Alfol 1214 (55% $C_{12}$, 40% $C_{14}$) n-alkyl alcohol (0.025 g-mole) mixed with 0.54 g potassium hydroxide, which was contained in a 200 cm$^3$ 3-neck glass flask. The reactant molar stoichiometry was therefore 10.4:1 glycidol:alcohol.

During the addition of the glycidol solution, the reaction mixture was well-stirred and was maintained at a temperature of 150°–155° C. via an oil bath. The methyl ethyl ketone solvent was distilled out continuously during the reaction and removed via a slow nitrogen gas purge.

After all of the glycidol solution had been added, the product remaining in the reaction flask was stripped (0.5 hr) of volatiles using the nitrogen purge, yielding 11.9 g of colored, semi-solid product. The yield of product was only 72%, based on the alcohol employed. Assay of the product by NMR spectroscopy indicated an average molecular weight of 660, equivalent to a 6:1 mole adduct of glycidol to alcohol.

EXAMPLE 6

Example 6 illustrates the method of this invention, in which the crude glycidol is predissolved in a non-polar solvent. The procedure employed in this example, as in Comparative Example C, was essentially that of Example I of U.S. Pat. No. 3,719,636 except that the glycidol employed was again crude glycidol (80% glycidol, 20% glycerine).

This example differed from Comparative Example C (and from Example I of U.S. Pat. No. 3,719,636) in that a non-polar solvent, toluene, was substituted for the polar solvent, methyl ethyl ketone, used previously.

An excess of crude glycidol (80% glycidol, 20% glycerine) was contacted with 180 g toluene and vigorously agitated to solubilize the glycidol. The mixture separated into two layers, with the upper toluene layer weighing 180.4 g and analyzing, by weight, as 88.7% toluene, 10.7 glycidol and 0.6% glycerine. An additional 20 g toluene was added to this separated toluene layer to yield a glycidol solution which contained 19.4 g of glycidol (0.26 g-mole) and 1.0 g glycerine in 180 g toluene.

The glycidol solution was added dropwise, over a period of 2.5 hours, to 4.9 g Alfol 1214 (55% $C_{12}$, 40% $C_{14}$) n-alkyl alcohol (0.025 g-mole) mixed with 0.54 g potassium hydroxide, which was contained in a 200 cm$^3$ 3-neck glass flask. The reactant molar stoichiometry was therefore 10.4:1 glycidol:alcohol.

The reaction mixture was well-stirred during the glycidol addition and was maintained at a temperature of 150°–155° C., via an oil bath. The toluene solvent was distilled out continuously during the reaction and removed via a slow nitrogen gas purge.

After all of the glycidol solution had been added, the product remaining in the reaction flask was stripped of volatiles using the nitrogen purge, yielding 21.2 g of clear, pale yellow semi-solid product. The yield of product was 92.4%, based on the alcohol employed. Assay of the product by NMR spectroscopy indicated an average molecular weight of 930, equivalent to a 10:1 mole adduct of glycidol to alcohol.

A comparison of the degree of polymerization for the surfactant product from Comparative Example C and that of Example 6 suggests that the glycerine present in the crude glycidol/MEK solution utilized in the Comparative Example caused undesirable side reactions which interfered with the glycidol polymerization. In the method of this invention, however, the use of the non-polar solvent apparently avoided all such adverse side reactions when crude glycidol was reacted with the n-alkyl alcohol.

The characteristics of the surfactant products made in Comparative Example C and in Example 6 are noted in Table I-a. These surfactant products were evaluated further, for their detersive properties, after each had been purified via the hexane extraction technique utilized in Example I of Wotjowicz, U.S. Pat. No. 3,719,636. Detersive properties of the two purified surfactant products were determined from their foaming characteristics, measured by the Ross-Miles Test. Values of foam height and foam half-life measurements for each of the two surfactant products are summarized in Table I-b and demonstrate the clear superiority of the Example 6 product over the Comparative Example C material.

This invention being thus described, it will be obvious that the same may be varied in many ways. Such variations are not to be regarded as a departure from the spirit and scope of the invention, and all such modifications are intended to be included within the scope of the following claims.

TABLE I-a

SURFACTANT PRODUCT CHARACTERISTICS

| Source of Compound Tested | Glycidol: Alcohol Reactant Molar Ratio | Av. Mol. Weight | Av. Degree of Polymerization | Reaction Efficiency (Based on Alcohol) |
|---|---|---|---|---|
| Example 1 | 3:1 | 468 | 3.8 | 90% |
| Example 2 | 6:1 | 769 | 7.8 | 89% |
| Example 3 | 3:1 | 520 | 3.8 | 89% |
| Example 4 | 3:1 | 470 | 3.8 | 89% |
| Comparative Example A | 3:1 | 438 | 3.4 | 57% |
| Comparative Example B | 10.4:1 | 926 | 10.2 | 58% |
| Comparative Example C | 10.4:1 | 660 | 6.1 | 72% |
| Example 6 | 10.4:1 | 930 | 10.1 | 92% |

TABLE I-b

DETERSIVE PROPERTIES OF 0.01% SURFACTANT SOLUTIONS

| Source of Compound Tested | Foam Height mm Initial | Foam Height mm After 5 Min. | Foam Half-Life (sec.) | Surface Tension (23.5° C.) Dynes/cm |
|---|---|---|---|---|
| Example 1 | 55 | 55 | 3300 | 29.0 |
| Example 2 | 35 | 35 | 3500 | 34.3 |
| Example 3 | 40 | 40 | 3227 | 30.0 |
| Example 4 | 47 | 47 | 3547 | 30.0 |
| Commercially produced 1 to 4 adduct of lauryl alcohol and ethylene oxide | 15 | 15 | 1100 | 30.0 |
| Comparative Example A | 20 | 20 | 1500 | 30.0 |
| Comparative Example B | 25 | 25 | 2200 | 32.6 |
| Comparative Example C | 40 | 40 | 1260 | * |
| Example 6 | 135 | 135 | 1620 | * |

*not measured

I claim:

1. A process for preparing n-alkyl glyceryl ether alcohols of the general formula:

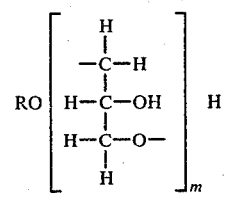

wherein R is a $C_{10}$–$C_{20}$ n-alkyl radical and m is a number from 1 to about 10, which comprises the steps of bringing together and reacting a $C_{10}$–$C_{20}$ n-alkyl primary alcohol and crude glycidol which is predissolved in a non-polar, non-reactive and miscible solvent selected from the group consisting of benzene, toluene, ortho-xylene, meta-xylene, para-xylene and mesitylene, in the presence of a basic catalyst in a reaction zone, said alcohol and glycidol being brought together and reacted in a molecular ratio within the range of from about 1:0.9 to about 1:10; maintaining the resulting reaction mass in an agitated condition; maintaining the temperature of the reaction mass within the range of from about 125° to about 180° C. during the reaction period; separating said non-polar solvent from the reaction mass; and recovering a $C_{10}$–$C_{20}$ n-alkyl glyceryl ether alcohol product.

2. The process of claim 1 wherein the non-polar non-reactive and miscible solvent is toluene.

3. The process of claim 1 wherein the n-alkyl alcohol reactant is a $C_{12}$–$C_{16}$ n-alkyl alcohol.

4. The process of claim 1 wherein the n-alkyl alcohol reactant is lauryl alcohol.

5. The process of claim 1 wherein the n-alkyl alcohol reactant is myristyl alcohol.

6. The process of claim 1 wherein the temperature of the reaction mass is maintained within the range of from about 150° to about 170° C.

7. The process of claim 1 wherein the reaction of the n-alkyl alcohol and glycidol is carried out in an inert atmosphere.

8. The process of claim 1 wherein the solution of glycidol in the non-polar solvent, is a 10–20 weight percent solution.

9. The process of claim 1 wherein the basic catalyst is potassium hydroxide.

10. The process of claim 1 wherein the crude glycidol contains at least 1% by weight glycerine.

11. The process of claim 1 wherein the crude glycidol contains from 1 to 25% by weight glycerine.

12. The process of claim 1 wherein the crude glycidol contains from 5 to 20% by weight glycerine.

13. The process of claim 1, 10, 11 or 12 wherein the crude glycidol also contains water.

* * * * *